United States Patent
Pham et al.

(10) Patent No.: US 9,282,888 B2
(45) Date of Patent: Mar. 15, 2016

(54) DIGITAL MEASUREMENT SYSTEM AND METHOD FOR OPTICAL APPLICATIONS

(75) Inventors: Mai Ngoc Pham, Elk Grove, CA (US); Hoa Dang Nguyen, Cider Hills, TX (US)

(73) Assignee: VSP Labs, Inc., Rancho Cordova, CA (US)

( * ) Notice: Subject to any disclaimer, the term of this patent is extended or adjusted under 35 U.S.C. 154(b) by 403 days.

(21) Appl. No.: 13/454,163

(22) Filed: Apr. 24, 2012

(65) Prior Publication Data
US 2013/0278895 A1 Oct. 24, 2013

(51) Int. Cl.
| | |
|---|---|
| *A61B 3/10* | (2006.01) |
| *A61B 3/00* | (2006.01) |
| *A61B 3/11* | (2006.01) |
| *G02C 13/00* | (2006.01) |

(52) U.S. Cl.
CPC ... *A61B 3/11* (2013.01); *A61B 3/00* (2013.01); *A61B 3/10* (2013.01); *G02C 13/005* (2013.01)

(58) Field of Classification Search
CPC ...... G02C 13/003; G02C 13/005; G02C 1/00; A61B 3/10; A61B 3/11; A61B 3/111
USPC .......................... 351/200, 205, 206, 246, 247
See application file for complete search history.

(56) References Cited

U.S. PATENT DOCUMENTS

| | | | |
|---|---|---|---|
| 2003/0123026 A1 | 7/2003 | Abitbol et al. | |
| 2004/0004633 A1 | 1/2004 | Perry et al. | |
| 2006/0132485 A1 | 6/2006 | Milinusic | |
| 2009/0051871 A1 | 2/2009 | Warden et al. | |
| 2010/0103516 A1 | 4/2010 | McKnight et al. | |
| 2010/0150991 A1 | 6/2010 | Bernstein | |
| 2010/0195045 A1* | 8/2010 | Nauche et al. | 351/204 |
| 2010/0220285 A1* | 9/2010 | Simmonds | 351/204 |
| 2010/0314446 A1 | 12/2010 | Morley, Jr. | |
| 2011/0242481 A1 | 10/2011 | Wada | |
| 2011/0267578 A1 | 11/2011 | Wilson | |
| 2012/0088581 A1 | 4/2012 | Mao et al. | |
| 2013/0060241 A1 | 3/2013 | Haddad | |

(Continued)

FOREIGN PATENT DOCUMENTS

| | | |
|---|---|---|
| JP | 2007206211 A | 8/2007 |
| KR | 100937367 B1 | 1/2010 |

OTHER PUBLICATIONS

International Search Report, dated Nov. 28, 2014, from corresponding International Application No. PCT/US2014/050717.

(Continued)

*Primary Examiner* — Scott J Sugarman
*Assistant Examiner* — Robert E Tallman
(74) *Attorney, Agent, or Firm* — Brient Globerman, LLC

(57) ABSTRACT

A digital measurement system and method for optical applications including a mobile client device having a digital camera and an audio port, and a laser measurement device having a laser. The laser measurement device connected to the mobile client device and electrically connected to the audio port of the mobile client device. The mobile client device is configured to activate the laser at the same time as the digital camera is activated, and capture an image of a patient. The mobile client device is configured to access a measurement module to calculate position of wear measurements based on a location of a laser mark in the captured image.

22 Claims, 11 Drawing Sheets

(56) References Cited

U.S. PATENT DOCUMENTS

2013/0088490 A1 4/2013 Rasmussen et al.
2014/0192316 A1 7/2014 Krenik

OTHER PUBLICATIONS

Written Opinion of the International Searching Authority, dated Nov. 28, 2014, from corresponding International Application No. PCT/US2014/050717.

International Search Report, dated Aug. 12, 2013, from corresponding International Application No. PCT/US2013/038004.
Written Opinion of the International Searching Authority, dated Aug. 12, 2013, from corresponding International Application No. PCT/US2013/038004.
International Preliminary Report on Patentability, dated Oct. 28, 2014, from corresponding International Application No. PCT/US2013/038004.
Extended European Search Report, dated Oct. 30, 2015, from corresponding European Patent Application No. 13780620.4.

* cited by examiner

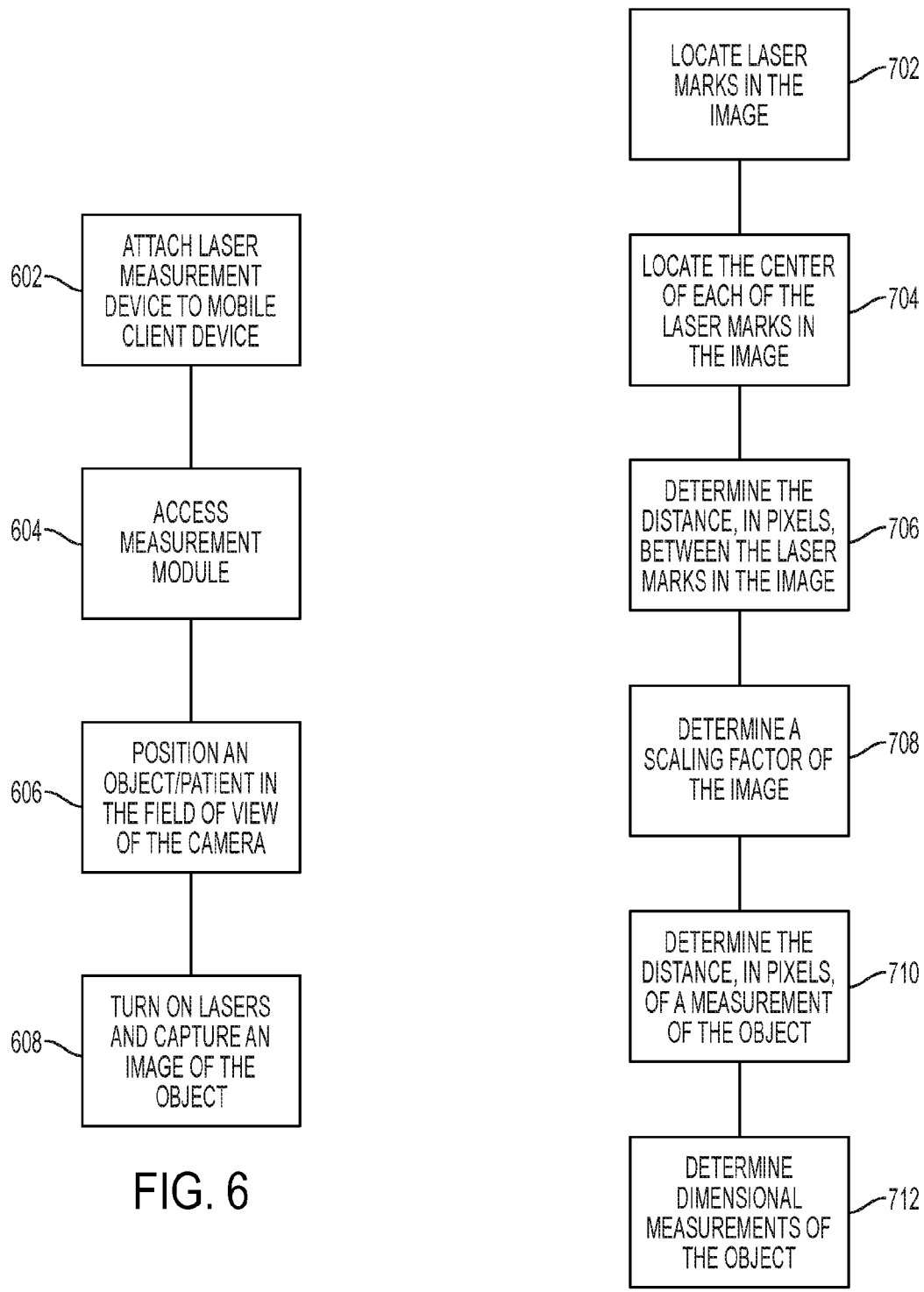

DIGITAL MEASUREMENT SYSTEM AND METHOD FOR OPTICAL APPLICATIONS

FIELD

The disclosure generally relates to eye care. More specifically, the disclosure relates to patient measurements for optical devices.

BACKGROUND

In general, eye care professionals (ECPs) prescribe lenses, fit lenses, and dispense prescriptions for eye correction to improve vision and to diagnose and treat various eye maladies. Lens prescriptions are typically determined using a refractor-head or test lenses that are positioned perpendicular to a patient's lines of sight. However, when the patient chooses a frame and the frame is fitted to the patient, the lenses are usually tilted based on the position of the frame. This tilt of the lenses can result in the prescription power being altered.

With the introduction of free form surfacing, also known as direct or digital surfacing, prescription lenses can be customized to a particular patient. Free form surfacing allows for complex surface shapes to be produced using computer numerically controlled (CNC) cutting tools and polishing machines.

Through the use of free form surfacing combined with accurate position of wear measurements, lenses can be customized to the patient's prescription, fitting geometry, and frame information. The position of wear is the position of the lens relative to the physical features of the actual patient. The position of wear is commonly measured in terms of vertex distance, pupillary distance, frame wrap, and pantoscopic tilt.

These measurements are generally taken using manual devices such as rulers, protractor type devices, distometers, and other manual devices or digital measurement devices. Current digital measurement devices are generally large stand alone devices that require the use of a separate reference sensor. In general, the current digital measurement devices require the patient's frames to be fit to the patient and the reference sensor must be positioned correctly on the fitted frames. If the reference sensor is not correctly positioned on the fitted frames, the measurement accuracy can be compromised.

SUMMARY

The digital measurement system and method for optical applications disclosed herein provides a mobile client device for obtaining patient measurements and/or position of wear measurements. The mobile client device may be implemented within and connected to a network of computer systems, for example, in a cloud computing infrastructure. This allows the mobile client device to access a measurement module and one or more databases to perform various functions, including calculating and determining measurements based on an image of a patient wearing a frame without using a reference sensor connected the frame.

In an illustrative embodiment, the system includes a mobile client device in communication with a computing infrastructure allowing the mobile client device to access a measurement module. The mobile client device includes a digital camera and an audio port. A laser measurement device having a laser is connected to the mobile client device, and electrically connected to the audio port of the mobile client device. The mobile client device is configured to activate the laser, for example, by transmitting an audio signal via the audio port to the laser measurement device, when the digital camera is activated to capture an image including a mark made by the laser within the image.

The laser measurement device may include a first laser and a second laser. The first laser and the second laser are positioned parallel with respect to one another a fixed distance apart. In an illustrative embodiment, the laser measurement device is positioned on a top portion of the mobile client device with the first laser and the second laser positioned on opposite sides of the digital camera.

In an illustrative embodiment, a method for obtaining digital measurements includes sending, by a mobile client device, an audio signal to activate a laser and capturing, by the mobile client device, an image of a patient wearing a selected frame at the same time as the laser is activated. The mobile client device accesses a measurement module. The measurement module is configured to analyze the captured image and determine a position of wear measurement, for example, a monocular pupillary distance (PD), a binocular PD, a monocular near PD, a binocular near PD, a vertex distance, a pantoscopic tilt, and other measurements of the type of the patient wearing the selected frame based on a location of a mark made by the laser in the captured image. The mobile client device may also store the position of wear measurement in a database.

In an illustrative embodiment, the mobile client device may submit an order for a frame and lenses to an ophthalmic laboratory including the position of wear measurement(s). The ophthalmic laboratory may use the position of wear measurement(s) to produce customized lenses for the patient.

In an illustrative embodiment, a method for obtaining digital measurements for optical applications includes locating, by a measurement module, a first laser mark created by a first laser and a second laser mark created by a second laser within a digital image. The measurement module determines a distance between the first laser mark and the second laser mark, in terms of a number of pixels. Since an actual distance between the first laser and the second laser is fixed, the measurement module determines a scaling factor for the digital image using the actual distance between the first laser and the second laser and the distance, in pixels, between the first laser mark and the second laser mark. Using the scaling factor, the measurement module determines one or more position of wear measurements of a patient from the digital image.

In an illustrative embodiment, the measurement module determines a monocular PD of the patient by determining a distance in pixels between an eye of the patient and a bridge of a nose of the patient in the digital image, and multiplying the distance, in pixels by the scaling factor. The measurement module determines a binocular PD of the patient by determining a distance in pixels between a center of each eye of the patient in the digital image, and multiplying the distance, in pixels, by the scaling factor. The measurement module determines a vertex distance by determining a distance in pixels between a back surface of a lens being worn by the patient and a front of a cornea of the patient in the digital image, and multiplying the distance, in pixels, by the scaling factor. The measurement module determines a pantoscopic tilt by determining an angle between a plane of a frame front and a frontal plane of a face of the patient in the digital image using distance measurements and calculations of a triangle.

In an illustrative embodiment, the measurement module determines a distance between a patient and a digital camera used to capture an image of the patient. On one embodiment, the distance is determined based on a focal length of the digital camera, a horizontal pixel position of a first mark made by a laser in the captured image, and the actual distance between the laser and the digital camera.

BRIEF DESCRIPTION OF THE DRAWINGS

The systems and methods disclosed herein are illustrated in the figures of the accompanying drawings which are meant to be exemplary and not limiting, in which like references are intended to refer to like or corresponding parts, and in which:

FIG. 6 illustrates a method of using the mobile client device and the laser measurement device;

FIG. 7 illustrates a flow diagram of a method for obtaining dimensional measurements;

DETAILED DESCRIPTION

Detailed embodiments of a digital measurement system and method for optical applications are disclosed herein, however, it is to be understood that the disclosed embodiments are merely exemplary of the systems and methods, which may be embodied in various forms. Therefore, specific functional details disclosed herein are not to be interpreted as limiting, but merely as a basis for the claims and as a representative basis for teaching one skilled in the art to variously employ the systems and methods disclosed herein.

Generally, the systems and methods disclosed herein include and are implemented within a computer system, network of computer systems, and/or cloud computing infrastructure having one or more databases and other storage apparatuses, servers, computers, and additional components, for example, processors, modems, terminals and displays, computer-readable media, algorithms, modules, and other computer-related components. The computer systems and/or computing infrastructure are especially configured, programmed, and adapted to perform the functions and processes of the systems and methods as disclosed herein.

Communications between components in the systems and methods disclosed herein may be unidirectional or bidirectional electronic communication through a wired or wireless configuration or network. For example, one component may be wired or networked directly, indirectly, through a third party intermediary, wirelessly, over the Internet, or otherwise with another component to enable communication between the components.

Figure 1:
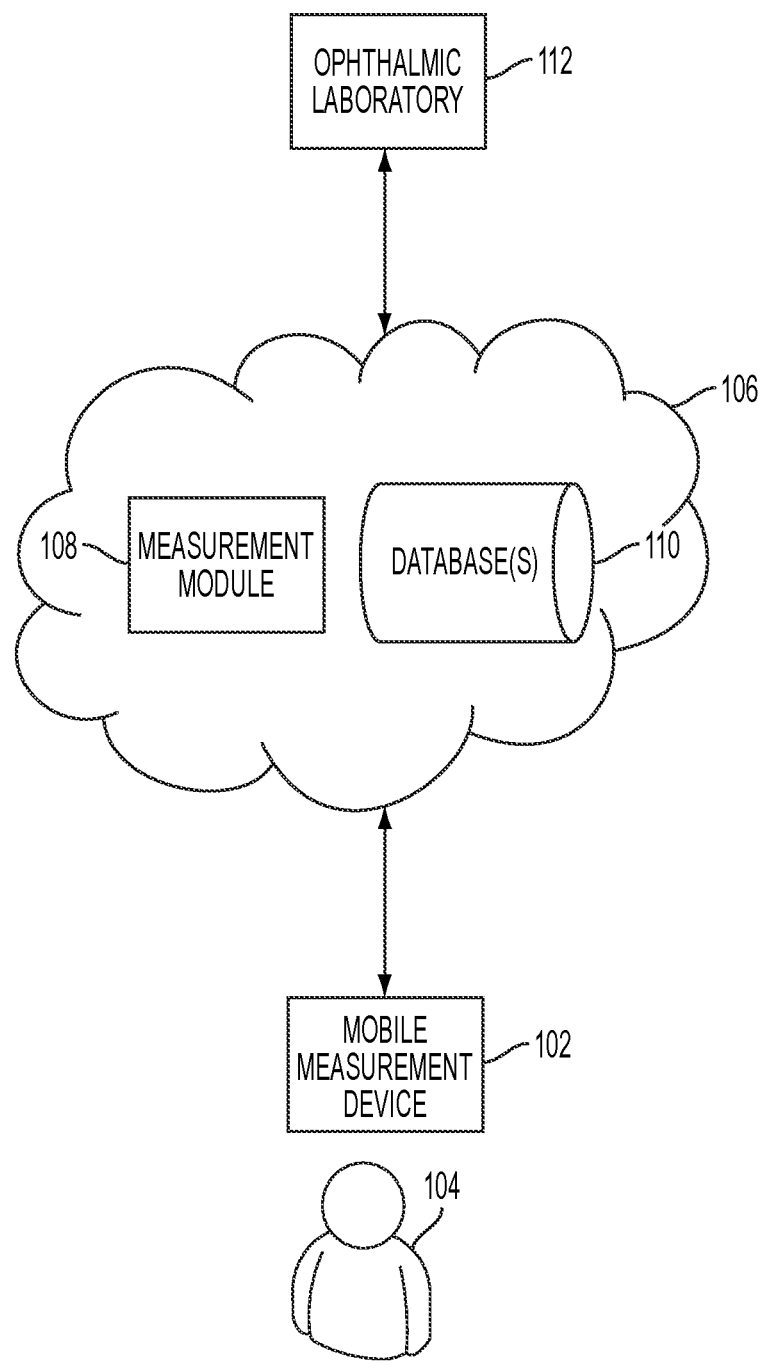
FIG. 1 illustrates an overview of the digital measurement system and method for optical applications.

An overview of the digital measurement system and method for optical applications according to an illustrative embodiment is described with reference to FIG. 1. As illustrated in FIG. 1, the system includes at least one mobile client device 102 configured to receive or collect data of or from at least one user 104, which may be a patient or an eye care professional (ECP), for example, an optometrist, an optician, an assistant, or other eye care technician. The mobile client device 102 includes an optical system and image acquisition technology. The optical system and image acquisition technology may be one or more digital cameras or digital video recorders capable of collecting one or more images, videos, or taking one or more photographs.

In an illustrative embodiment, the mobile client device 102 communicates with, accesses, receives data from, and transmits data to a computing infrastructure 106. In general, the computing infrastructure 106 provides computing/processing resources, software, data access, and storage resources without requiring the user or client to be familiar with the location and other details of the computing infrastructure 106. The computing infrastructure 106 includes one or more modules accessible by the mobile client device 102, including a measurement module 108 and one or more associated databases 110. In an illustrative embodiment, the mobile client device 102 may communicate with one or more ophthalmic laboratories 112 via the computing infrastructure 106 to submit orders to the one or more ophthalmic laboratories 112 for frames and/or lenses.

In an illustrative embodiment, the mobile client device 102 accesses the measurement module 108 allowing accurate position of wear measurements of a patient to be obtained based on one or more images of the patient. The mobile client device 102 can be used to obtain, for example, monocular pupillary distance (PD), binocular PD, monocular near PD, binocular near PD, vertex distance, wrap angle, pantoscopic tilt, and other measurements of the type. These measurements may then be sent to and used, for example, by the one or more ophthalmic laboratories 112 to produce customized lenses for the patient.

Figure 2A:
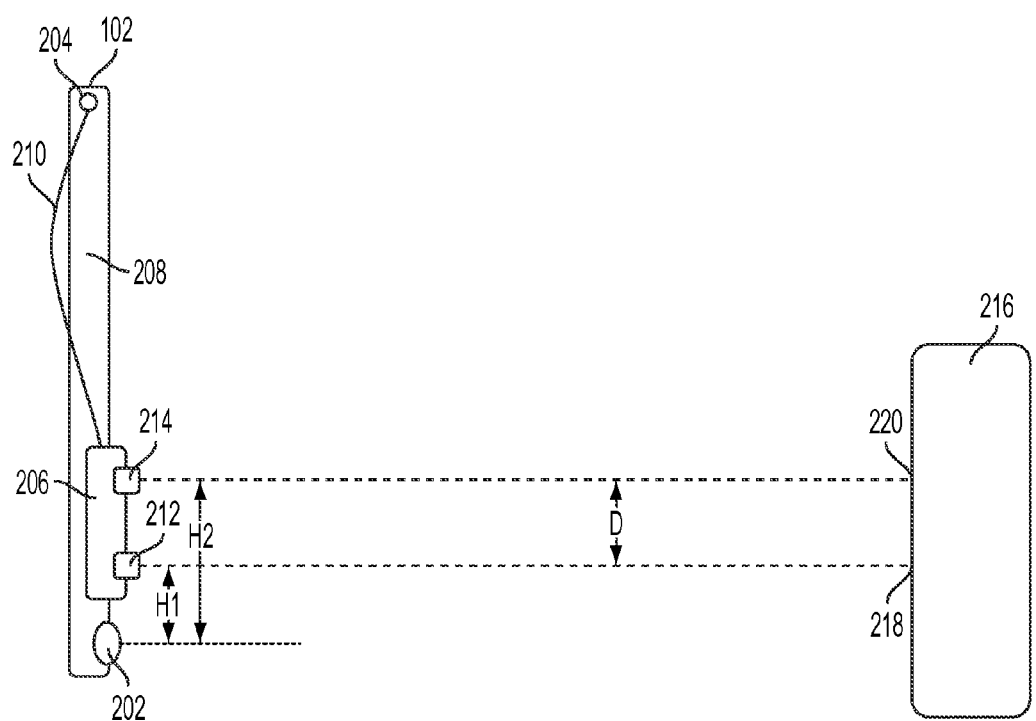
FIG. 2A illustrates a top view of a mobile client device including a laser measurement device of the digital measurement system.
Figure 2B:
FIG. 2B illustrates a side view of the mobile client device including the laser measurement device of the digital measurement system.

A mobile client device 102 according to an illustrative embodiment is described with reference to FIGS. 2A and 2B. As illustrated in FIGS. 2A and 2B, the mobile client device 102 is a tablet computing device. The mobile client device 102 includes one or more digital cameras and/or digital video recorders 202. The mobile client device 102 also includes one or more audio ports 204. The one or more audio ports 204 may be, for example, 3.5-mm stereo headphone minijacks, and other audio ports of the type.

In an illustrative embodiment, the mobile client device 102 is an Apple® iPad®, for example, but not limited to a first generation/version, a second generation/version, and other generations/versions of the Apple® iPad®. The Apple® iPad® includes a 3.5-mm stereo headphone minijack (for example, the audio port 204). The second generation Apple® iPad® includes a first digital camera/digital video recorder (for example, the digital cameras and/or digital video recorders 202) on the back of the Apple® iPad®, and a second digital camera/digital video recorder on the front of the Apple® iPad® (not shown). The first digital camera/digital video recorder 202 on the back of the Apple® iPad® is capable of video recording, HD (720p) up to 30 frames per second with audio and has a still camera with 5× digital zoom. The second digital camera/digital video recorder on the front of the Apple® iPad® is capable of video recording, VGA up to 30 frames per second with audio and has a VGA-quality still camera.

In an illustrative embodiment, a laser measurement device 206 is connected to the mobile client device 102. The laser measurement device 206 may be mounted on or removably connected to the mobile client device 102. As illustrated, the laser measurement device 206 is positioned on a first side or a top portion 208 of the mobile client device 102 proximal to the digital camera and/or digital video recorder 202 of the mobile client device 102. The laser measurement device 206 is electrically connected to the mobile client device 102 via the audio port 204. In an illustrative embodiment, the laser measurement device 206 includes wiring 210 including an audio plug configured to be received in and electrically connected to the audio port 204 of the mobile client device 102.

The laser measurement device 206 includes a first visible light, red dot low power laser 212 and a second visible light, red dot low power laser 214. The first and second visible light, red dot low power lasers, 212 and 214, respectively, may be the same lasers or different lasers. In an illustrative embodiment, the first and second lasers 212 and 214, respectively, have a wavelength of about 650 nm and an output power of less than about 1 MW. One example of the first and second lasers 212 and 214, respectively, is part number LC-LMD-650-03-01-A from Laser Components, a distributer and manufacturer of laser products located in Olching, Germany.

As illustrated in FIG. 2A, the first and second lasers 212 and 214, respectively, are spaced apart by a distance D, as measured from the center of the first laser 212 to the center of the second laser 214, and are in parallel alignment with respect to one another. The center of the first laser 212 is positioned a distance H1 from the center of the digital camera and/or digital video recorder 202, and the center of the second laser 214 is positioned a distance H2 from the center of the digital camera and/or digital video recorder 202.

Figure 3:
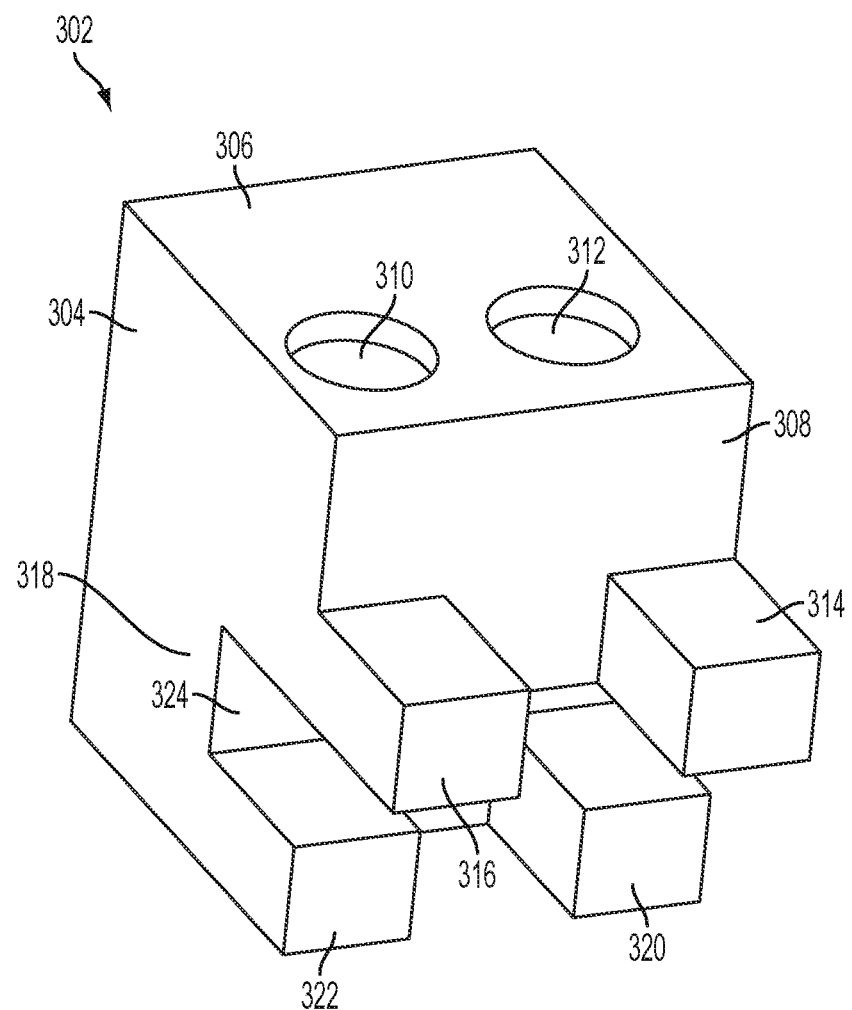
FIG. 3 illustrates an embodiment of a laser measurement device.
Figure 4:
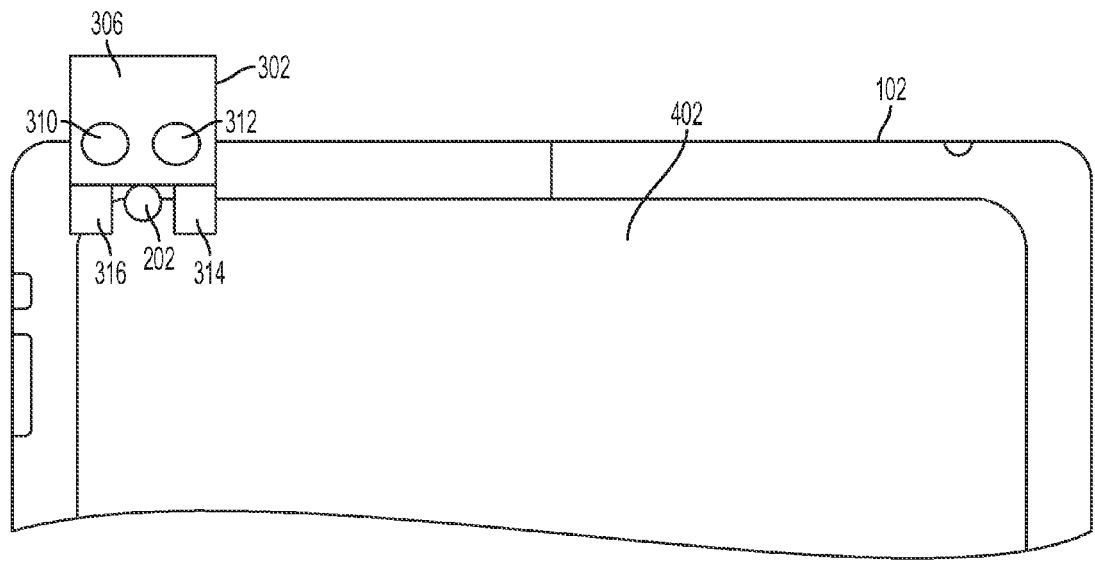
FIG. 4 illustrates an embodiment of the laser measurement device of FIG. 3 attached to the mobile client device.

Another embodiment of a laser measurement device is describe with reference to FIGS. 3 and 4. As illustrated in FIG. 3, a laser measurement device 302 includes an outer housing 304 having a front face 306 and a bottom 308. A first laser 310 and a second laser 312, which may be the same as the first and second lasers 212 and 214, respectively, are positioned within the outer housing 304 on the front face 306 of the laser measurement device 302. As illustrated, the first laser 310 and the second laser 312 are positioned next to each other, horizontally along the front face 306, and are in parallel alignment with one another.

A first support 314 and a second support 316 are attached to or monolithically formed with the outer housing 304 and protrude vertically downward from the bottom 308 or are perpendicular to the bottom 308. As illustrated, the first support 314 and the second support 316 are aligned with one another, horizontally along the bottom 308. The laser measurement device 302 also includes an extended portion 318 attached to or monolithically formed with the outer housing 304 opposite the front face 306 of the outer housing 304. A third support 320 and a fourth support 322 are attached to or monolithically formed with the outer housing 304 and protrude vertically downward from the extended portion 318 or are perpendicular to the extended portion 318. The outer housing 304 and the supports 314, 316, 320, and 322 form a notch 324 between the outer housing 304 and the third support 320 and the fourth support 322, between the first support 314 and the third support 320, and between the second support 316 and the fourth support 322. The laser measurement device 302 also includes wiring including an audio plug configured to be received in and electrically connected to the audio port 204 of the mobile client device 102.

Referring to FIG. 4, the laser measurement device 302 may be placed on the top of the mobile client device 102. As illustrated in FIG. 4, the mobile client device 102 is received in the notch 324 of the laser measurement device 302 and the top of the mobile client device 102 contacts the extended portion 318 of the laser measurement device 302. The first support 314 and the second support 316 engage a back portion 402 of the mobile client device 102 and the third support 320 and the fourth support 322 engage a front portion of the mobile client device 102.

As illustrated in FIG. 4, the laser measurement device 302 is positioned on the mobile client device 102 allowing the digital camera 202 of the mobile client device 102 to be unobstructed. In an illustrative embodiment, the laser measurement device 302 is positioned with the first support 314 and the third support 320 on one side of the digital cameral 202 and the second support 316 and the fourth support 322 on an opposite side of the digital cameral 202.

In an illustrative embodiment, the first laser 310 and the second laser 312 have a diameter of about $21/64$ inches. The front face 306 measures about 1 inch by 1 inch. The length of the outer housing 304 is about 1.5 inches. The length of the extended portion 318 is about $37/64$ inches. The first support 314 and the second support 316 extend about $41/64$ inches from the bottom 308, and the third support 320 and the fourth support 322 extend about $7/8$ inches from the extended portion 318. The recess 324 has a length of about $19/64$ inches. The first support 314 and the second support 316, and the third support 320 and the fourth support 322 are spaced apart by a distance of about 0.3 to about 0.4 inches, to allow for the digital cameral 202 of the mobile client device 102 to be positioned therebetween.

Although, the laser measurement device 302 is described as having certain dimensions, it should be appreciated by those skilled in the art that the various dimensions may be modified accordingly, for example, increased or decreased, to adapt the laser measurement device to various mobile client devices 102 and various other applications.

The laser measurement devices 206 and 302 also include control circuitry enclosed within an outer housing of the laser measurement devices 206 and 302 for controlling the first laser 212/310 and the second laser 214/312. In an illustrative embodiment, the laser measurement device 206/302 is activated by receiving an audio signal from the mobile client device 102 via the audio port 204. A circuit diagram of the control circuitry of the laser measurement device 206/302 according to an illustrative embodiment is described with reference to FIG. 5. The mobile client device 102 controls the laser measurement device 206/302 by sending a signal, for example, a 10 khz sine wave, through the audio port 204. The laser measurement device 206/302 detects the audio signal and uses the audio signal to control the operation of the first laser 212/310 and the second laser 214/312.

Figure 5:
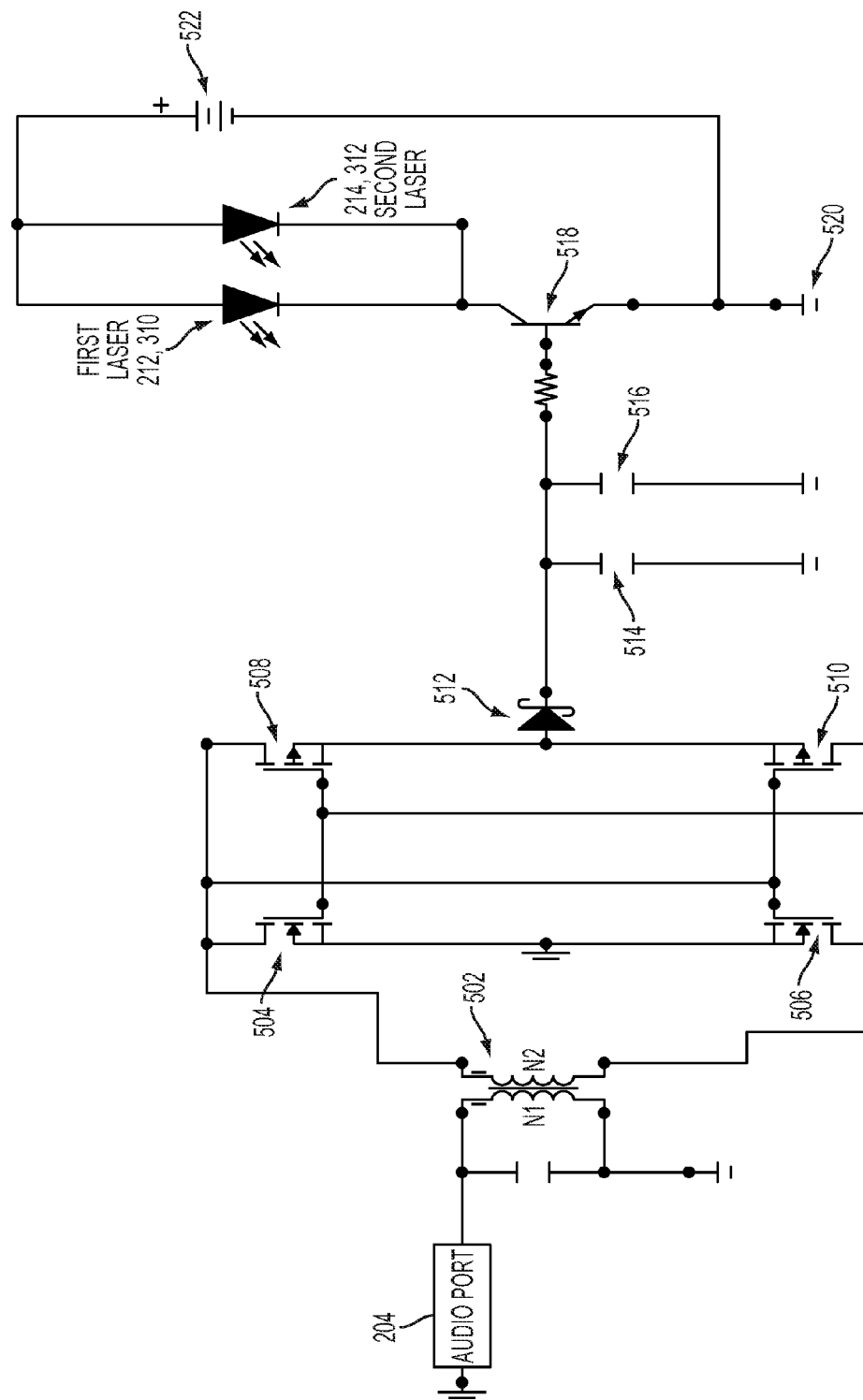
FIG. 5 illustrates a circuit diagram of the laser measurement device of the digital measurement system.

As illustrated in FIG. 5, the signal travels to a transformer 502. The transformer 502 steps up the voltage of the signal. The signal is then rectified by a field-effect transistor (FET) bridge made up of four FETs, 504-510. The rectified signal travels to a blocking diode 512. The blocking diode 512 is used to keep capacitors 514 and 516 from feeding back into the FETs, 504-510. The capacitors 514 and 516 filter the rectified signal into a direct current (DC) voltage. This DC voltage turns on a transistor 518 which activates the first and second lasers (212 and 214) by providing a ground path 520. In an illustrative embodiment, the first laser 212/310 and the second laser 214/312 are powered by a power source 522. In an illustrative embodiment, the power source 522 is, for example, two replaceable LR44 button batteries, however, it should be appreciated by those skilled in the art that the first laser 212/310 and the second laser 214/312 may be powered by one or more additional or alternative batteries, the mobile client device 102, and/or other power sources of the type. Under normal operation the first laser 212/310 and the second laser 214/312 are only activated for a short period of time. When the two replaceable LR44 button batteries are used as the power source 522, the two replaceable LR44 button batteries will generally last about several months to about five years.

A method of using the mobile client device 102 and the laser measurement device 206/302 according to an illustrative embodiment is described with reference to FIGS. 1-4 and 6. As illustrated, the user 104 attaches the laser measurement device 206/302 to the mobile client device 102, illustrated as 602. In an illustrative embodiment, the user 104 attaches the laser measurement device 206/302 to the mobile client device 102 by connecting the laser measurement device 206/302 to the top of the mobile client device 102 and electrically connecting the laser measurement device 206/302 to the mobile client device 102 by connecting the audio plug to the audio port 204 of the mobile client device 102.

The user 104 accesses the measurement module 108 via the mobile client device 102, illustrated as 604. In an illustrative embodiment, the mobile client device 102 is configured to transmit an audio signal, for example, a 10 khz audio signal, via the audio port 204 when the digital camera 202 is activated by the user 104. The laser measurement device 206/302 connected to the audio port 204 receives the audio signal. This causes the laser measurement device 206/302 to turn on for a short period of time, for example, about 100 milliseconds to about 300 milliseconds, when the digital camera 202 is activated in a similar manner as a flash of a camera operates.

The user 104 positions a patient wearing a selected frame or an object, for example, illustrated as 216 in FIGS. 2A and 2B, in the field of view of the digital camera 202, illustrated as 606. The user 104 then simultaneously turns on the laser measurement device 206/302 and captures one or more images of the patient or object on the mobile client device 102, for example, on a screen or display of the mobile client device 102, illustrated as 608. The captured image may be stored, for example, in a memory of the mobile client device 102 and/or in the one or more databases 110. In an illustrative embodiment, the user 104 presses or touches a button on the mobile client device 102 to activate the digital camera 202 and capture the image(s) of the patient or object. When the user 104 activates the digital camera 202, the laser measurement device 206/302 turns on simultaneously as the digital camera 202 captures the image(s). The first laser 212/310 and the second laser 214/312, create a first mark and a second mark, for example, illustrated as 218 and 220 in FIG. 2A, on the patient or object in the captured image.

A method of obtaining dimensional measurements according to an illustrative embodiment is described with reference to FIGS. 1-4 and 7. The measurement module 108 analyzes the captured image(s) and locates the first mark and the second mark created by the first laser 212/310 and the second laser 214/312 within the captured image, 702. The measurement module 108 locates the center of each of the first mark and the second mark created by the first laser 212/310 and the second laser 214/312 within the captured image, 704, using known image processing technology and/or algorithms. In an illustrative embodiment, the measurement module 108 locates the center of each of the first mark and the second mark by filtering and analyzing the captured image. The filtering process involves a combination of Gaussian blur, custom color channel manipulation, intensity thresholding, and a Suzuki85 algorithm for connected component labeling. The filtering process produces a set of points defining possible marks created by the first laser 212/310 and the second laser 214/312 or laser mark candidate shapes. The set of points or shapes is analyzed according to several criteria, such as, but not limited to, shape area, dimensions of a rectangle bounding the shape, and the existence of a similar shape within a certain distance threshold from the shape. If the aforementioned shapes meet the above criteria, the shapes are considered to be successful matches.

The measurement module 108 then determines the distance between the first mark and the second mark created by the first laser 212/310 and the second laser 214/312 within the captured image, 706. In an illustrative embodiment, the distance between the first mark and the second mark created by the first laser 212/310 and the second laser 214/312 within the captured image is determined in terms of pixels.

Referring to FIG. 2A, the first laser 212 and the second laser 214 are spaced the distance D, for example, 16 mm, apart and are parallel with respect to one another. Therefore, the actual distance between the center of the first mark and the center of the second mark created by the first laser 212 and the second laser 214 within the captured image should be the distance D, for example, 16 mm. Referring to FIG. 7, using the distance D and the distance between the first mark and the second mark in pixels, the measurement module 108 determines a scaling factor for the captured image, 708. The measurement module 108 determines a distance in pixels of a measurement of the patient or object, illustrated as 710. Using the scaling factor, the measurement module 108 determines the actual dimensional measurements of the measurement of the patient or object captured in the image, 712.

One example of a measurement calculation of a dimensional measurement of an object is described herein. The distance D between the centers of the first laser 212 and the second laser 214 is 16 mm. The distance between the first mark and the second mark in pixels or pixel distance is determined to be 47 pixels. The scaling factor is D divided by the pixel distance, which is about 0.34 mm/pixels (16 mm/47 pixels=about 0.34 mm/pixels). Thus, the actual distance between two selected points in the captured image, for example, a distance between the patient's pupils, can be determined by determining the distance between the two selected points in pixels and multiplying the distance between the two selected points in pixels by the scaling factor. For example, if the distance between the two selected points in the captured image is 141 pixels the actual distance between the two selected points is 47.94 mm (141 pixels×0.34 mm/pixels=47.94 mm).

Figure 8:
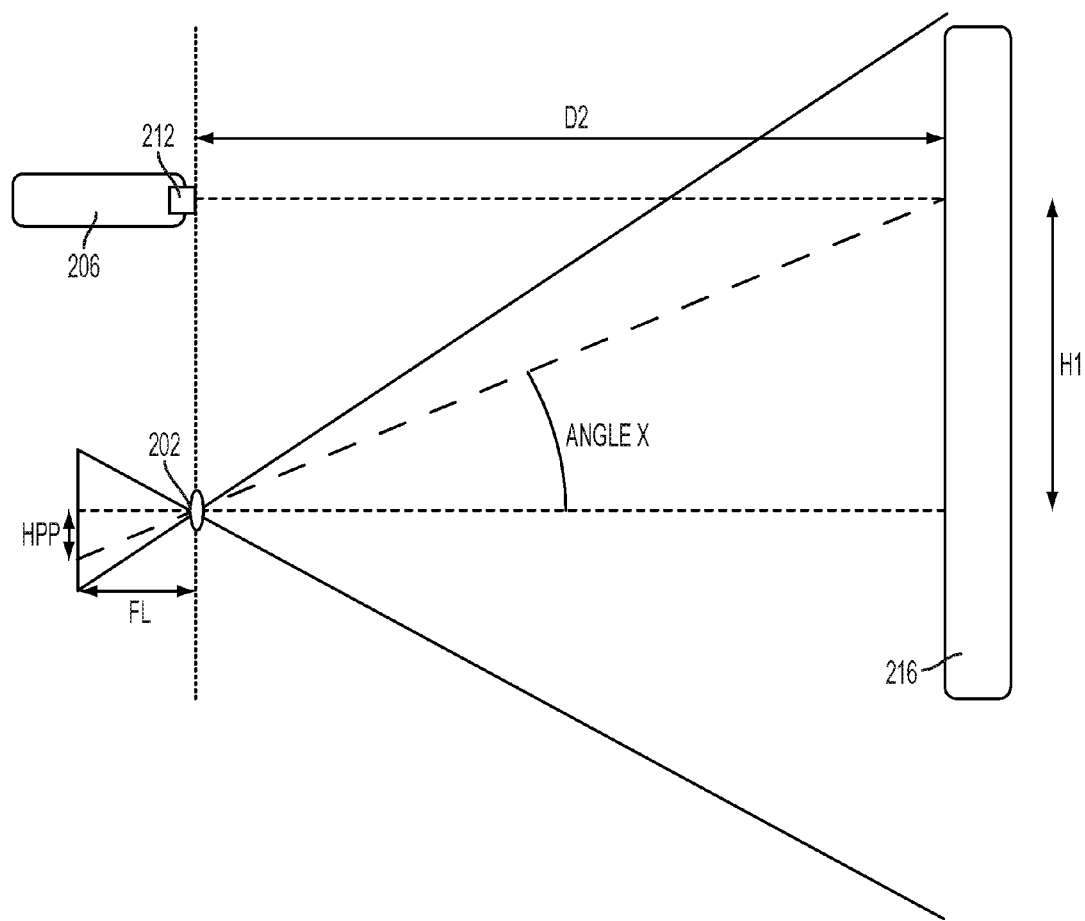
FIG. 8 illustrates a schematic for obtaining a distance measurement.
Figure 9:
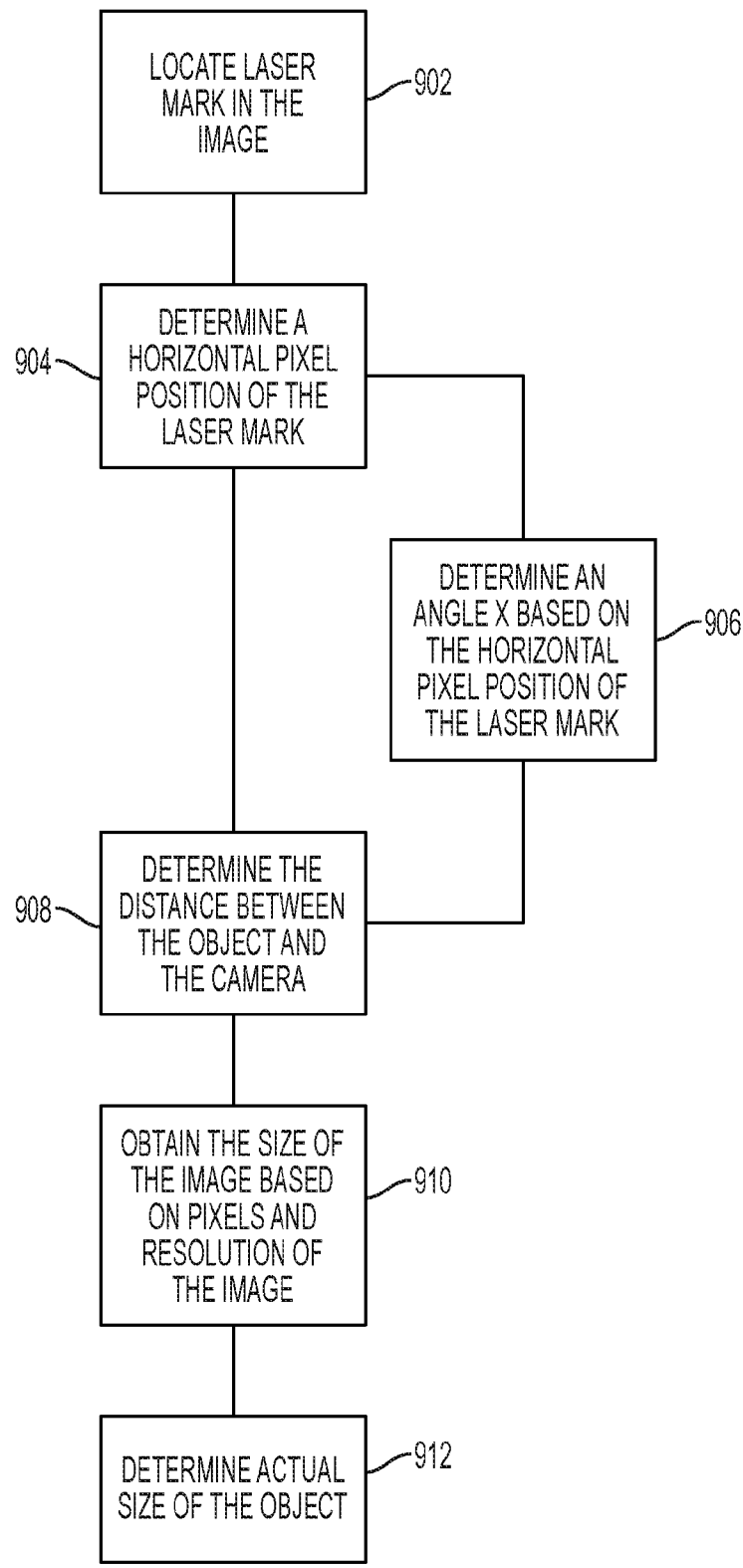
FIG. 9 illustrates a flow diagram of a method for obtaining a distance measurement.
Figure 10:
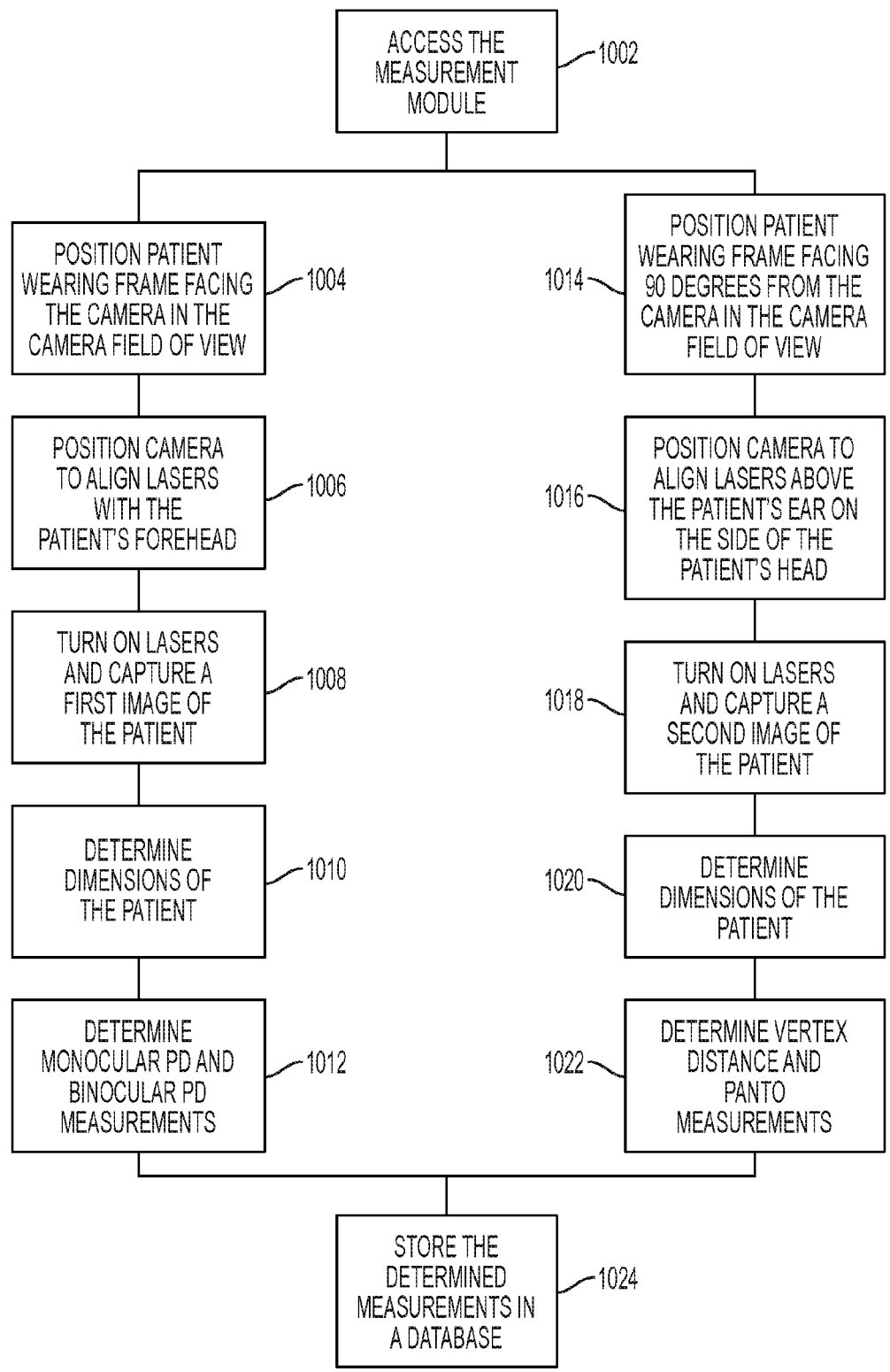
FIG. 10 illustrates a flow diagram of a method for obtaining position of wear measurements of a patient.

A method of obtaining a distance measurement according to an illustrative embodiment is described with reference to FIGS. 8 and 9. The measurement module 108 analyzes the captured image(s) and locates at least one of the first mark and the second mark created by the first and second lasers 212 and 214, respectively, within the captured image, 902. As illustrated in FIG. 8, only the first laser 212 is illustrated, however it should be appreciated by those skilled in the art that either one of the lasers 214, 310, or 312 may be used in the following method.

As illustrated in FIG. 8, the location of the first mark created by the first laser 212 within the captured image changes based on a distance D2 of the object 216 from the digital camera 202. As the distance D2 increases, an angle X decreases and the position of the first mark in the field of view of the digital camera 202 changes. The measurement module 108 may allow the user 104 to select the type of mobile client device 102 being used, for example the Apple® iPad®. The Apple® iPad® camera has a focal length (FL) of about 531 pixels. Referring to FIGS. 8 and 9, the measurement module 108 determines a horizontal pixel position (HPP) distance of the first mark relative to a center of the digital camera 202, illustrated as 904. The measurement module 108 may determine the angle X from the center line of the digital camera 202 to the position of the first mark based on the HPP and FL, illustrated as 906. Since the distance H1 between the first laser 212 and the digital camera 202 is known, the measurement module 108 determines the distance D2 between the object 216 and the digital camera 202, illustrated as 908. The distance D2 may be determined using the distance H1 and the angle X, or using the distance H1, the focal length FL, and the distance HPP.

One example of a distance calculation is described with reference to FIG. 8. The focal length FL of the digital camera 202 is 531 pixels. The distance H1 between the first laser 212 and the digital camera 202 is 30 mm. The HPP is determined by the measurement module 108 to be 40 pixels. The angle $X=\tan^{-1}(HPP/FL)$. The distance $D2=H1/\tan(\text{angle } X)$. Combining the formula for the angle X and the formula for the distance D2, $D2=(H1\times FL)/HPP$. Using the formula for the angle X, the angle X is calculated to be about 4.31 degrees ($\tan^{-1}(40 \text{ pixels}/531 \text{ pixels})=4.31$ degrees). The distance D2 is calculated to be about 398.25 mm (30 mm/tan(4.31)=398.25 mm). Alternatively, using the combined formula, D2 is calculated to be about 398.25 mm ((30 mm×531 pixels)/40 pixels=398.25 mm).

In an other illustrative embodiment, the laser measuring device 206/302 may include a light receiver. The laser measuring device 206/302 may measure the time required for at least one of a first laser beam and a second laser bean created by the first laser 212/310 and the second laser 214/312, respectively, to travel to a patient or an object, reflect off of the patient or object, and travel back to the light receiver. By measuring the time for the at least one of a first laser beam and a second laser bean created by the first laser 212/310 and the second laser 214/312 to be received by the light receiver, the distance (for example, D2) between the digital camera 202 and the patient or object can be determined.

Once the distance D2 is determined, the measurement module 108 can determine the actual size of the patient or object based on the captured image. Referring back to FIG. 9, the mobile client device 102 obtains the size of the image based on the number of pixels and the resolution of the digital camera 202, illustrated as 910. Based on the size of the image and the distance D2, the measurement module 108 can determine the actual size of the patient or object, illustrated as 912.

Referring to FIGS. 1-4 and 10, the mobile client device 102 with the laser measurement device 206/302 attached, as described above, may be used to obtain, for example, monocular pupillary distance (PD), binocular PD measurements, vertex distance, and pantoscopic tilt (panto) measurements of a patient from one or more images of the patient wearing a selected frame. In general, the ECP fits the frame to the patient prior to taking the one or more images of the patient.

As illustrated, the user 104 accesses the measurement module 108 via the mobile client device 102, illustrated as 1002. In order to obtain or calculate the monocular PD, which is the distance from each of the patient's pupils, using light reflected from the cornea, to the center of the patient's nose where the center of the frame bridge rests, and the binocular PD, which is the distance between the patient's pupils, the patient should be facing the digital camera 202 or mobile client device 102. The user 104 then positions the patient wearing the selected frame, with the patient facing the digital camera 202 or mobile client device 102 in the field of view of the digital camera 202, illustrated as 1004.

The user 104 also positions the digital camera 202 or mobile client device 102 to cause the first laser 212/310 and the second laser 214/312 to align with the patient's forehead or other substantially flat portion of the patient's head, 1006. The mobile client device 102 controls the first laser 212/310 and the second laser 214/312 so that the first laser 212/310 and the second laser 214/312 are only on during a very brief time when the image is captured. Since the first laser 212/310 and the second laser 214/312 are low power and are only on briefly, the first laser 212/310 and the second laser 214/312 should be minimally noticeable to the patient. This also means there should be no danger to the eyes of the patient when the first laser 212/310 and the second laser 214/312 are activated.

With the digital camera 202 or mobile client device 102 positioned the user 104 simultaneously activates the first laser 212/310 and the second laser 214/312 and captures a first image of the patient, for example, by pressing a button on the mobile client device 102, illustrated as 1008. Once the mobile client device 102 captures the first image of the patient, the measurement module 108 analyzes the first image, for example using facial recognition and 3-D rendering technology, and determines the size and dimensions of the patient, for example, as described above with reference to FIGS. 7-9, illustrated as 1010. The measurement module 108 then analyzes the image and determines or calculates the monocular PD and the binocular PD measurements of the patient, 1012.

In an example, using the method described above with reference to FIG. 7, the distance D between the centers of the first laser and the second laser is 16 mm, and the measurement module 108 determines the distance between the first mark and the second mark in the first image in pixels or a pixel distance to be 47 pixels. The scaling factor is D divided by the pixel distance, which is about 0.34 mm/pixels (16 mm/47 pixels=about 0.34 mm/pixels). The monocular PD is determined by determining the distance from each of the patient's pupils to the center of the patient's nose. In this example, the measurement module 108 determines the pixel distance from the center of the patient's right pupil to the center of the patient's nose in the first image to be 70 pixels, and the pixel distance from the center of the patient's left pupil to the center of the patient's nose in the first image to be 70 pixels. The measurement module 108 determines the patient's monocular PD by multiplying the pixel distances by the scaling factor. The patient's monocular PD for the right eye is 23.8 mm (70 pixels×0.34 mm/pixels=23.8 mm), and the patient's monocular PD for the left eye is 23.8 mm (70 pixels×0.34 mm/pixels=23.8 mm).

The binocular PD is determined by determining the distance between the centers of each of the patient's pupils. In this example, the measurement module 108 determines the pixel distance between the centers of each of the patient's pupils in the first image to be 140 pixels. The measurement module 108 determines the patient's binocular PD by multiplying the pixel distance by the scaling factor. The patient's binocular PD is 47.6 mm (140 pixels×0.34 mm/pixels=47.6 mm)

In order to obtain or calculate the vertex distance, which is the distance between the back surface of a lens and the front of the cornea of the patient, and the pantoscopic tilt, which is the angle between the plane of the lens and frame front and the frontal plane of the face, the patient should be facing about ninety degrees away from the digital camera 202 or mobile client device 102. The user 104 positions the patient wearing the selected frame, with the patient facing about ninety degrees away from the digital camera 202 or mobile client device 102, in the field of view of the digital camera 202, illustrated as 1014.

The user 104 also positions the digital camera 202 or mobile client device 102 to cause the first laser 212/310 and the second laser 214/312 to align with the side of the patient's head above the patient's ear or other substantially flat portion of the patient's head, 1016. The user 104 simultaneously activates the first laser 212/310 and the second laser 214/312 and captures a second image of the patient, 1018. The measurement module 108 analyzes the second image, for example, using facial recognition and 3-D rendering technology, and determines the size and dimensions of the patient, for example, as described above with reference to FIGS. 7-9, illustrated as 1020. The measurement module 108 then analyzes the image and determines or calculates the vertex distance and pantoscopic tilt measurements of the patient wearing the selected frames 1022.

In an example, using the method described above with reference to FIG. 7, the distance D between the centers of the first laser and the second laser is 16 mm, and the measurement module 108 determines the distance between the first mark and the second mark in the second image in pixels or a pixel distance to be 47 pixels. The scaling factor is D divided by the pixel distance, which is about 0.34 mm/pixels (16 mm/47 pixels=about 0.34 mm/pixels). The vertex distance is determined by determining the distance between a back surface of a lens and a front of a cornea of the patient. In this example, the measurement module 108 determines the pixel distance from the back surface of the lens to the front of the cornea of the patient's eye in the second image to be 15 pixels. The measurement module 108 determines the vertex distance by multiplying the pixel distance by the scaling factor. The vertex distance is 5.1 mm (15 pixels×0.34 mm/pixels=5.1 mm).

The pantoscopic tilt is determined by determining an angle between a plane of the lens and frame front and a frontal plane of the patient's face. In this example, the frontal plane of the patient's face is vertical, and the plane of the lens and frame front is tilted, for example, creating a hypotenuse (Hyp.) of a right triangle with a height of the right triangle or an adjacent side (Adj.) of the right triangle being the frontal plane of the patient's face. A horizontal distance from the frontal plane of the patient's face to the plane of the lens and frame front creates an opposite side of the right triangle. The lengths of the hypotenuse and the adjacent side are the respective distances from the opposite side of the right triangle to a point where the frontal plane of the patient's face and the plane of the lens and frame front intersect. The measurement module 108 can determine the length in pixels of each of the sides of the right triangle. In this example, the measurement module 108 determines the pixel length of the adjacent side to be 12 pixels, and the pixel length of the hypotenuse of the right triangle to be 12.1 pixels. The measurement module 108 then determines the pantoscopic tilt by calculating the inverse cosine of the pixel length of the adjacent side divided by the pixel length of the hypotenuse (pantoscopic tilt=$\cos^{-1}$(Adj./Hyp.)). The pantoscopic tilt is 7.3 degrees ($\cos^{-1}$(12/12.1) =7.3 degrees). It should be appreciated that the method of calculating the pantoscopic tilt measurement described above is one of many ways to calculate the pantoscopic tilt, and that the pantoscopic tilt measurement may be calculated using various other geometry type calculations known in the art.

The measurement module 108 may store the monocular PD, binocular PD, vertex distance, pantoscopic tilt, and other measurements in the one or more databases 110, illustrated as 1024. In an illustrative embodiment, the measurements are stored in association with the patient's personal information allowing the patient's specific measurements to be retrieved by the user 104 via the mobile client device 102 if desired.

Figure 11:
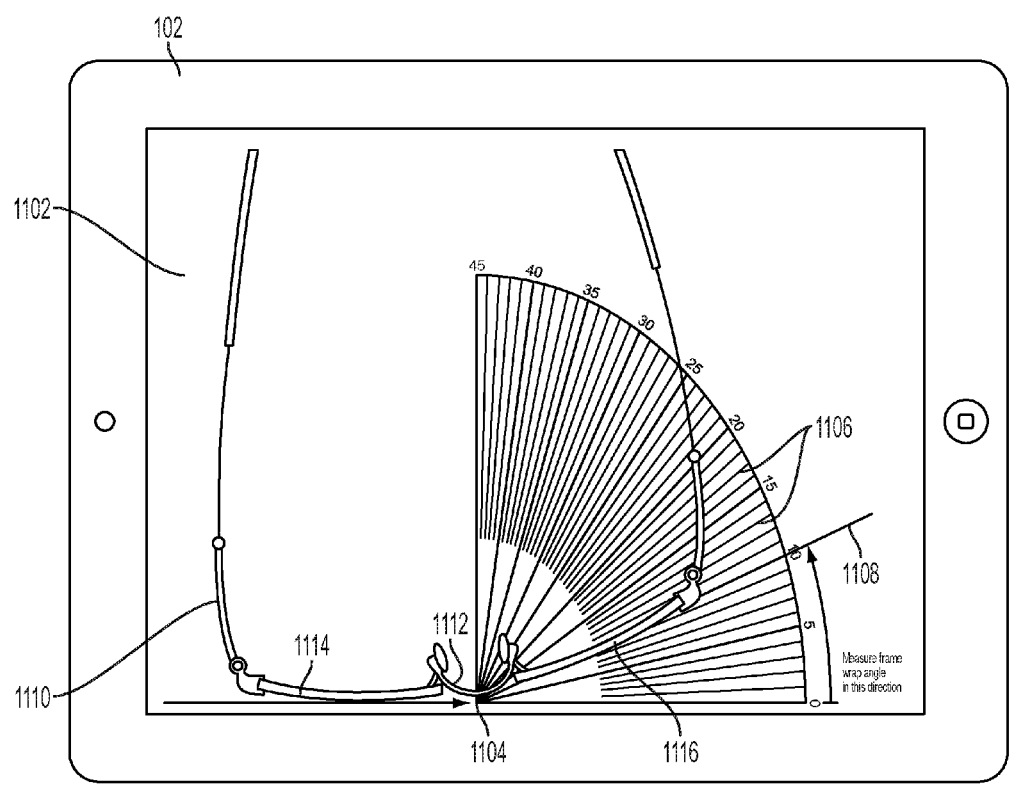
FIG. 11 illustrates an embodiment of an interactive frame wrap measurement tool displayed on the mobile client device.

In an illustrative embodiment, the mobile client device 102 may also be used to determine a frame wrap measurement of the selected frames. A frame wrap measurement tool on the mobile client device 102 according to an illustrative embodiment is described with reference to FIG. 11. As illustrated in FIG. 11, the measurement module 108 also includes a frame wrap measurement tool 1102 that may be displayed on the mobile client device 102. The frame wrap tool 1102 includes a center point 1104 and a number of angular measurement lines 1106 extending from the center point 1104 at varying angles, for example, beginning at a zero degree angle and ending at a forty-five degree angle with angular measurement lines 1106 for each incremental degree therebetween.

The frame wrap measurement tool 1102 also includes an interactive measurement line 1108 having a pivot point at the center point 1104. The interactive measurement line 1108 extends from the center point 1104 and is movable by the user 104 to align with each of the various angular measurement lines 1106. In an illustrative embodiment, the mobile client device 102 includes a touch-screen display and the user 104 moves or positions the interactive measurement line 1108 by, for example, stylus or touch, and pivoting the interactive measurement line 1108 to align with a desired angular measurement line 1106. In another illustrative embodiment, the user 104 moves or positions the interactive measurement line 1108 by clicking on and pivoting the interactive measurement line 1108 using a computer mouse or other computer device.

To measure the frame wrap measurement of a selected frame 1110, the user 104 accesses the frame wrap measurement tool 1102 of the measurement module 108. The frame wrap measurement tool 1102 is then displayed on the mobile client device 102, for example, on the touch-screen display of the mobile client device 102. The user 104 places the selected frame 1110 on the touch-screen display of the mobile client device 102 and aligns the center of a bridge 1112 of the selected frame 1110 with the center point 1104 of the frame wrap measurement tool 1102. The user 104 also aligns a first lens 1114 of the selected frame 1110 parallel to the zero degree angular measurement line. A second lens 1116 of the selected frame 1110 will be aligned parallel to one of the various angular measurement lines 1106 of the frame wrap measurement tool 1102. The user 104 then pivots the interactive measurement line 1108 to align parallel to the second lens 1116 of the selected frame 1110. The interactive measurement line 1108 will align with one of the angular measurement lines 1106 indicating a frame wrap angle or frame wrap measurement of the selected frame 1110.

The measurement module 108 may store the frame wrap measurement in the one or more databases 110. Similarly, the frame wrap measurement may be stored in association with the patient's personal information allowing the frame wrap measurement of the frame selected by the patient to be retrieved by the user 104 via the mobile client device 102 if desired.

In an illustrative embodiment, the monocular PD, binocular PD, vertex distance, pantoscopic tilt, and frame wrap measurements may then be sent to the one or more ophthalmic laboratories 112 along with a patient's frame and lens order via the mobile client device 102. The one or more ophthalmic laboratories 112 may use the measurements to produce customized lenses for the patient. For example, the one or more ophthalmic laboratories 112 may use the measurements and the patients prescription to determine a compensated prescription for the patient's lenses based on the selected frames and the patient's position of wear measurements.

In an illustrative embodiment, the mobile client device 102 may be in communication with a practice management interface (PMI) or practice management system/software (PMS), for example, Compulink by Compulink Business Systems, Inc. of Westlake Village, Calif., MaximEyes by First Insight-Optometry of Hillsboro, Oreg., OfficeMate by Eyefinity, Inc. of Rancho Cordova, Calif., or AcuityLogic by Eyefinity, Inc. of Rancho Cordova, Calif., and other PMIs/PMSs of the type. In an illustrative embodiment, the mobile client device 102 is integrated into the PMI. In this illustrative embodiment, the mobile client device 102 is configured to collect data, receive data, and transmit data within the PMI, for example, patient information, frame information, lens information, and the measurements obtained/calculated as described above.

In an illustrative embodiment, the mobile client device 102 may be continually or periodically connected to the computing infrastructure 106 or separate/disconnected from the computing infrastructure 106. The network may be a local area network or a wide area network and may be a private or public network of any size or scope. In an illustrative embodiment, the network is the Internet. Although the module 108 is described as being in the computing infrastructure 106, the module 108 may be included within the mobile client device 102 or different functions of the module 108 may be distributed between the computing infrastructure 106 and mobile client device 102.

In an illustrative embodiment, the mobile client device 102 may allow the user 104 to interact with the mobile client device 102, receive, and/or collect data from the user 104 through the use of a client/user interface or graphical user interface, for example, an interface installed on the mobile client device 102, an application, and/or a remotely accessible interface. The user interface may include visual, audio, graphics, charts, and other features of the type. The user interface may include one or more menus incorporating a number of specific questions, prompts, selections/buttons, selection boxes, fillable fields, or any combination thereof that the user may answer, select, or input data into, for example by typed, stylus/touch-screen, oral, and/or written.

In an illustrative embodiment the mobile client device 102 may include one or more security features to prevent unauthorized users from using the mobile client device 102. The mobile client device 102 may require a user name and password, and/or other personal identification information, which can be used to identify and/or authenticate the user 104.

Although the mobile client device 102 is described above as being the Apple® iPad®, the mobile client device 102 may be a digital camera, a digital video recorder, or other mobile electronic communication device such as but not limited to a computer, a tablet computer, a smart phone, a personal digital assistant (PDA), and other mobile devices that can access, provide, transmit, receive, and modify information over wired or wireless networks, that contains the optical and image acquisition technology described above, and that is capable of receiving and using the laser measuring device described above. Further, the measurement module 108 may be platform agnostic and can be accessed by and run on various computing platforms.

Although the laser measurement devices 206 and 302 are described as plugging into the audio port 204 and being activated via an audio signal from the mobile client device 102, it should be appreciated by that those skilled in the art that the laser measurement devices 206 and 302 may be configured to plug into the mobile client device 102 using alternative means. Such alternative means may include, but are not limited to a universal serial bus (USB), and other means of the type. Further, although the laser measurement devices 206 and 302 are described as including two visible light, red dot low power lasers, it should be appreciated by that those skilled in the art that more than two lasers may be included, and that other types of lasers may be used instead of the visible light, red dot low power lasers.

Although the systems and methods disclosed herein may have been with reference to one of the laser measurement devices 206 or 302, it should be appreciated that either of the laser measurement devices 206 or 302 may be used in accordance with the systems and methods disclosed herein.

While the systems and methods have been described and illustrated in connection with certain embodiments, many variations and modifications will be evident to those skilled in the art and may be made without departing from the spirit and scope of the disclosure. The disclosure is thus not to be limited to the precise details of methodology or construction set forth above as such variations and modification are intended to be included within the scope of the disclosure. Moreover, unless specifically stated any use of the terms first, second, etc. do not denote any order or importance, but rather the terms first, second, etc. are merely used to distinguish one element from another.

We claim:

1. A method for obtaining digital measurements, comprising:
   sending, by a mobile client device, an audio signal to activate a laser;
   capturing, by said mobile client device, an image of a patient wearing a selected frame at the same time as said laser is activated; and
   accessing, by said mobile client device, a measurement module configured to determine a position of wear measurement of said patient wearing said selected frame based on a location of a mark made by said laser in said captured image.

2. The method of claim 1, further comprising storing, by said mobile client device, said position of wear measurement in a database.

3. The method of claim 1, further comprising submitting, by said mobile client device, an order to an ophthalmic laboratory including said selected frame and said position of wear measurement.

4. The method of claim 3, wherein said submitting said order includes submitting, by said mobile client device, said position of wear measurement including at least one of a monocular pupillary distance (PD), a binocular PD, a monocular near PD, a binocular near PD, a vertex distance, and a pantoscopic tilt.

5. The method of claim 1, wherein said position of wear measurement is one or more measurements selected from a group consisting of:
   a monocular pupil distance;
   a binocular pupil distance;
   a vertex distance; and
   a pantoscopic tilt.

6. A method for obtaining digital measurements, comprising:
   activating at least one laser that is operatively coupled to a processor;
   capturing, by a camera that is operatively coupled to said at least one laser, an image of a patient wearing a selected frame and one or more laser marks that are generated on the wearer when said at least one laser is activated; and calculating, by a processor, at least one position of wear measurement of a lens relative to the physical features of the patient based on said captured image and said one or more laser marks in the image.

7. The method of claim 6, wherein the step of calculating said at least one position of wear measurement of the lens relative to the physical features of the patient further comprises:
locating, by a processor, a first laser mark created by a first laser and a second laser mark created by a second laser within said captured image;
calculating, by a processor, a distance between said first laser mark and said second laser mark, said distance being a number of pixels; and
calculating, by a processor, a scaling factor for said captured image using an actual distance between said first laser and said second laser and said distance, in pixels, between said first laser mark and said second laser mark, wherein said position of wear measurement of the lens relative to the physical features of the patient is calculated using said scaling factor.

8. The method of claim 7, further comprising determining, by a processor, a distance in pixels between an eye of the patient and a bridge of a nose of the patient in said captured image.

9. The method of claim 8, further comprising multiplying, by a processor, said distance in pixels between the eye of the patient and the bridge of the nose of the patient by said scaling factor to determine a monocular pupil distance for the eye.

10. The method of claim 7, further comprising determining, by a processor, a distance in pixels between a center of each eye of the patient in said captured image.

11. The method of claim 10, further comprising multiplying, by a processor, said distance in pixels between the center of each eye of the patient by said scaling factor to determine the binocular pupil distance between the patient's eyes.

12. The method of claim 7, further comprising determining, by a processor, a distance in pixels between a back surface of the lens and a front of a cornea of the patient in said captured image.

13. The method of claim 12, further comprising multiplying, by a processor, said distance in pixels between the back surface of the lens and the front of the cornea of the patient by said scaling factor to determine a vertex distance.

14. The method of claim 7, further comprising determining, by a processor, an angle between a plane of a frame front and a frontal plane of a face of the patient in said captured image.

15. The method of claim 14, further comprising determining a distance between the patient and said camera.

16. The method of claim 6, further comprising the step of storing the calculated position of wear measurement in memory.

17. A method for obtaining digital measurements associated with a wearer wearing a selected eyeglass frame, comprising:
providing a first and second laser that is operatively coupled to a handheld computing device having a camera;
activating, by said handheld computing device, said first and second lasers so that a first and a second laser mark is projected onto the wearer;
capturing, using said handheld computing device, an image of the wearer wearing the selected eyeglass frame and said first and second laser marks; and
calculating, by said handheld computing device, at least one of a monocular pupil distance, a binocular pupil distance, a vertex distance, and a pantoscopic tilt at least partially based on a physical distance between said first and second lasers and a measured distance of said first and said second laser marks in said captured image.

18. The method of claim 17, further comprising submitting, by said handheld computing device, an order to an ophthalmic laboratory including said at least one of said monocular pupil distance, said binocular pupil distance, said vertex distance, and said pantoscopic tilt.

19. The method of claim 17, further comprising storing, by said handheld computing device, said at least one of said monocular pupil distance, said binocular pupil distance, said vertex distance, and said pantoscopic tilt in memory.

20. The method of claim 17, further comprising analyzing said captured image using facial recognition and three dimensional rendering techniques to determine the size and dimensions of the wearer's facial features.

21. The method of claim 17, wherein said first laser and said second laser are positioned parallel to one another such that a laser beam emitted from said first laser and a second laser beam emitted from said second laser are parallel to one another.

22. The method of claim 7, wherein said first laser and said second laser are positioned parallel to one another.

* * * * *